United States Patent [19]

Tanji et al.

[11] Patent Number: 5,429,632
[45] Date of Patent: Jul. 4, 1995

[54] DISPOSABLE DIAPERS

[75] Inventors: Hiroyuki Tanji; Ichiro Wada; Yoshio Ono; Hiroyuki Soga, all of Kawanoe, Japan

[73] Assignee: Uni-Charm Corporation, Ehime, Japan

[21] Appl. No.: 31,463

[22] Filed: Mar. 15, 1993

[30] Foreign Application Priority Data

Apr. 1, 1992 [JP] Japan .................. 4-080052

[51] Int. Cl.6 ........................................ A61F 13/15
[52] U.S. Cl. ........................... 604/385.2; 604/394; 604/395
[58] Field of Search ............... 604/364, 381, 382, 384, 604/385.1, 385.2, 393–398; 156/164, 496

[56] References Cited

U.S. PATENT DOCUMENTS

| | | | |
|---|---|---|---|
| 3,842,838 | 10/1974 | Gellert | 604/378 |
| 4,044,769 | 8/1977 | Papajohn | 604/397 |
| 4,662,887 | 5/1987 | Williams . | |
| 4,695,279 | 10/1987 | Steer | 604/397 |
| 4,704,116 | 11/1987 | Enloe | 604/385.2 |
| 4,892,536 | 1/1990 | DesMarais et al. | 604/385.2 |
| 4,900,318 | 2/1990 | Toth | 604/385.1 |
| 4,990,147 | 2/1991 | Freeland | 604/385.2 |
| 5,026,364 | 1/1991 | Robertson | 604/388.2 |
| 5,037,416 | 8/1991 | Allen et al. | 604/385.1 |
| 5,062,846 | 11/1991 | Holt et al. | 604/385.1 |
| 5,137,525 | 8/1992 | Glassman | 604/385.1 |
| 5,176,672 | 1/1993 | Bruemmer et al. | 604/385.1 |
| 5,204,997 | 4/1993 | Suzuki et al. | 604/385.1 |

FOREIGN PATENT DOCUMENTS

| | | | |
|---|---|---|---|
| 0241925 | 10/1987 | European Pat. Off. . | |
| 2572902 | 5/1986 | France . | |
| 2668364 | 4/1992 | France . | |
| 3186262 | 8/1991 | Japan | 604/385.2 |
| 3202057 | 9/1991 | Japan | 604/385.1 |
| 3207358 | 9/1991 | Japan | 604/385.2 |
| 3218751 | 9/1991 | Japan | 604/385.1 |
| 2255896 | 11/1992 | United Kingdom | 604/385.2 |

*Primary Examiner*—Randall L. Green
*Assistant Examiner*—K. M. Reichle
*Attorney, Agent, or Firm*—Lowe, Price, LeBlanc & Becker

[57] ABSTRACT

A disposable diaper so improved that an uppermost sheet 14 is formed at its central zone with an opening 16, first and second elastic members 17, 18 are attached to the sheet 14 along halves of the opening's periphery, respectively, with the longitudinally opposite ends of these elastic members intersecting each other at the longitudinally opposite ends of the opening 16, respectively, and the uppermost sheet 14 is torn off from these intersections.

2 Claims, 5 Drawing Sheets

DISPOSABLE DIAPERS

BACKGROUND OF THE INVENTION

This invention relates to a disposable diaper used to absorb and hold excretion from a human body.

Japanese Utility Model Application Disclosure Gazette No. 1974-120439 discloses a diaper cover having a topsheet formed at its central zone with an opening extending longer in the longitudinal direction of the topsheet than in the transverse direction thereof, wherein the opening is provided along its peripheral edge with a longitudinally stretchable elastic member so as to define a closed loop-shaped elastic line. Japanese Patent Application Disclosure Gazette No. 1986-41304 also discloses a disposable diaper having a topsheet formed at its central zone with an opening extending longer in the longitudinal direction than in the transverse direction of the topsheet, wherein the opening is provided along its laterally opposite side edges with elastic members, respectively.

With the above diaper cover and diaper both having openings, excretion flows through said opening into a pocket defined between said topsheet and another topsheet underlying the first-mentioned topsheet and is held therein. Accordingly, any skin disease which might appear when the user's skin is stained by excretion spreading over the uppermost topsheet can be reliably prevented and an unpleasant feeling can be alleviated.

From the viewpoint of public sanitation, it is desired to dispose of a used diaper after solid excrement sticking to the diaper has been scraped away in a water closet, and such practice for public sanitation is generally observed. With the previously mentioned well known diaper having an opening, however, it is difficult to scrape excrement away in a water closet since the excrement flows into said pocket.

Said operation of scraping solid excretion away may be facilitated by tearing off the upper most topsheet from the edge of said opening so as to expose most of the topsheet underlying said uppermost topsheet. However, it is difficult, when the opening has a peripheral edge which is elasticized by a continuous elastic member attached thereto in a closed loop-shape as in the diaper cover disclosed by said Japanese Utility Model Application Disclosure Gazette No. 1974-120439, to tear off the uppermost topsheet surrounding said opening unless a suitable tool such as knife or scissors is used. Due to such inconvenience, there is the danger that the diaper might be disposed of just like ordinary garbage with solid excretion remaining held therein or having been incompletely scraped away.

It is an object of the invention to provide a disposable diaper improved so that although the entire peripheral edge of said opening is elasticized by elastic members the uppermost topsheet can nevertheless be easily torn off from the edge so as to expose the other topsheet underlying said uppermost topsheet and thereby to facilitate said operation of scraping away.

SUMMARY OF THE INVENTION

The object set forth above is achieved, according to the invention, by a disposable diaper comprising an integral laminate composed of a liquid-permeable first topsheet, a liquid-impermeable backsheet, a liquid absorbent core sandwiched between said first topsheet and said backsheet, and a liquid-resistant second topsheet lying over said first topsheet, wherein said second topsheet is formed substantially at its central zone with an opening extending longer in the longitudinal direction than in the transverse direction of the second topsheet; wherein said second topsheet is bonded along its outer periphery to said first topsheet; and wherein longitudinally elastic members are attached onto said second topsheet along the peripheral edge of said opening, characterized by that:

said elastic members comprise first and second elastic members being not continuous with each other and substantially the entire periphery of said opening is elasticized by attaching these first and second elastic members along opposing halves of said periphery, respectively.

Preferably, the longitudinally opposite ends of said first and second elastic members intersect, contact or closely approach each other at the longitudinally opposite ends of said opening.

Preferably, said first and second elastic members are covered with the peripheral edge of said opening.

Preferably, each of said first and second elastic members utilizes at least one rubber thread.

Preferably, the edge portion of said opening adjacent which at least respective ones of the longitudinally opposite ends of said first and second elastic members are located is provided with a guide notch for tearing off.

Preferably, said second topsheet is made from nonwoven fabric and most of component fibers thereof are oriented in the direction along which said guide notch is to be torn off.

BRIEF DESCRIPTION OF THE DRAWINGS

The invention will be described by way of example in reference with the accompanying drawings, in which.

PREFERRED EMBODIMENTS OF THE INVENTION

Figure 1:
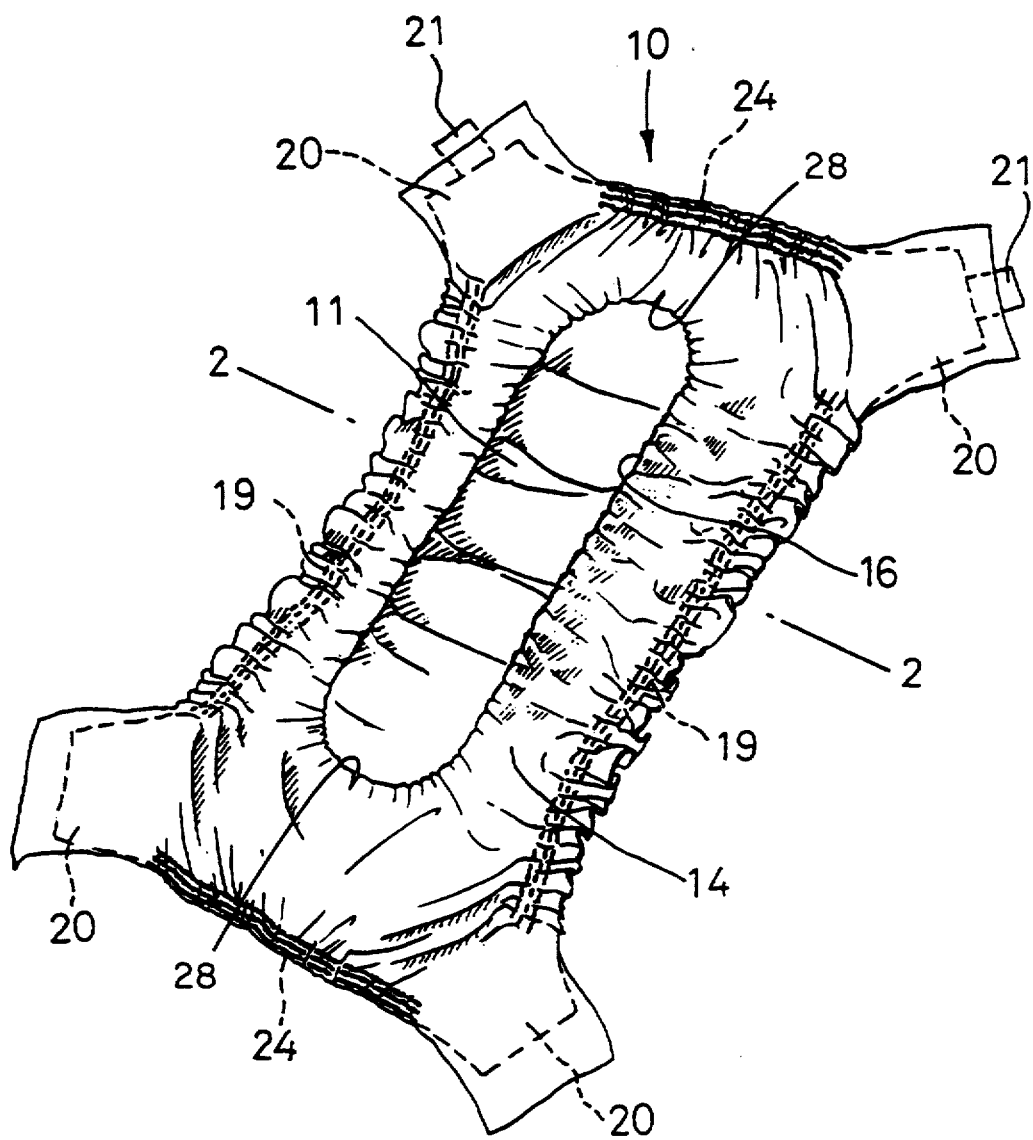
FIG. 1 is a perspective view showing the inner side of a disposable diaper constructed as an embodiment of the invention.
Figure 2:
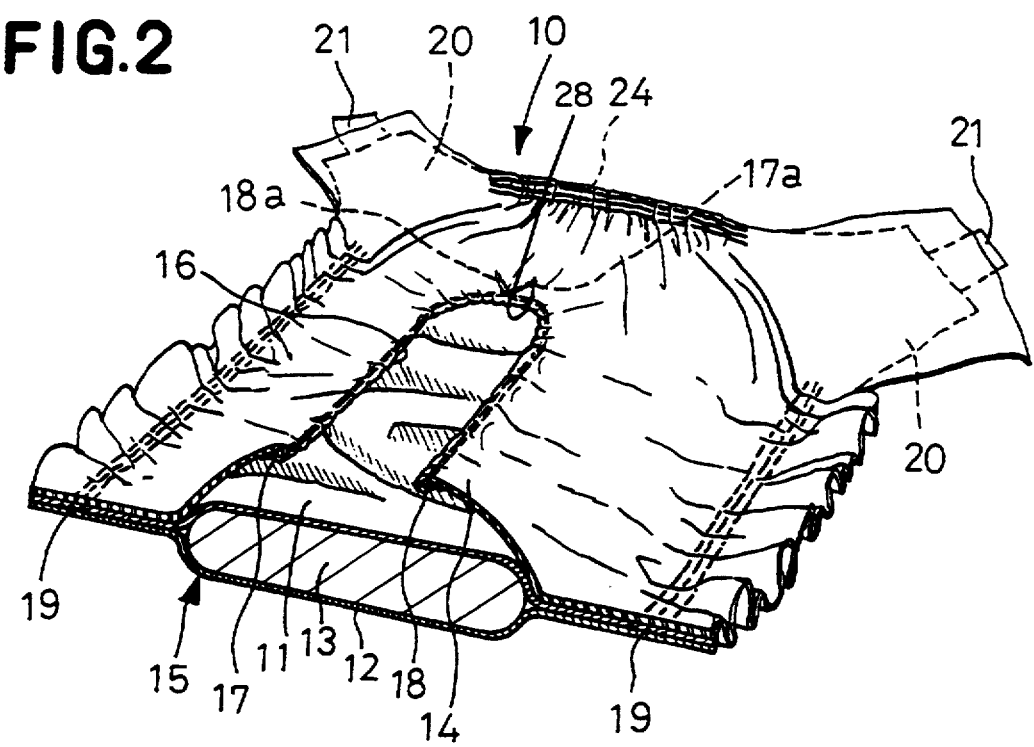
FIG. 2 is a perspective view showing this embodiment partially in a section taken along a line 2—2 in FIG. 1.
Figure 3:
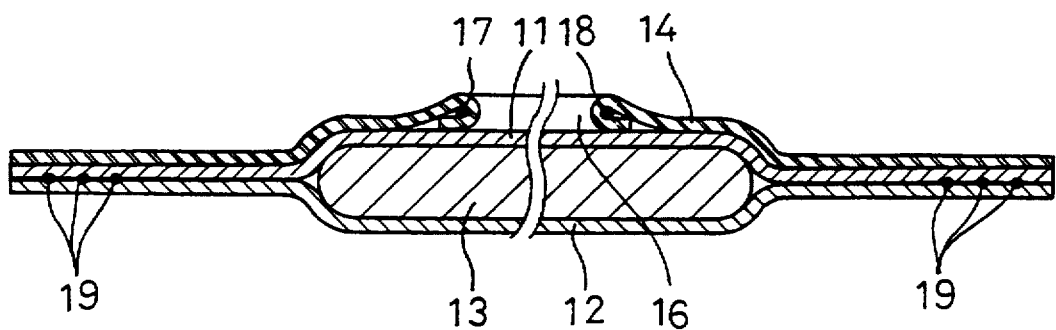
FIG. 3 is a sectional view showing this embodiment, in an enlarged scale, taken along the line 2—2 in FIG. 1.

Referring to FIGS. 1 and 2, a diaper 10 comprises an integral laminate 15 composed of a liquid-permeable first topsheet 11, a liquid-impermeable backsheet 12, a liquid-absorbent core 13 sandwiched therebetween, and a liquid-resistant second topsheet 14. The second topsheet 14 is centrally formed with an opening 16 which is longer in the longitudinal direction than in the transverse direction of top 14 and has longitudinally opposite ends describing circular arcs, respectively. The opening 16 may be formed at least within the crotch zone.

If the opening 16 is divided by an imaginary longitudinal center line in two, left and right halves of the opening 16 are provided along and adjacent their edges with longitudinally stretchable first and second elastic members 17, 18, respectively, with the use of hot melt type adhesive (not shown), wherein each of the first and second elastic members 17, 18 comprises a plurality of elastic threads. In the vicinity of the longitudinally opposite ends of the opening 16, longitudinally opposite ends 17a of the first elastic member 17 intersect the associated ends 18a of the second elastic member 18 (See FIGS. 2 and 4). In this manner, not only the entire peripheral edge of the opening 16 can be uniformly contracted under the effect of these elastic members 17, 18 so as to form gathers but also the intersecting ends of these elastic members 17, 18 can be easily separated from each other when the second topsheet 14 is to be torn off from locations adjacent these intersecting ends of the elastic members 17, 18 since they are not endless loop-like elastic members but merely intersect each other at their longitudinally opposite ends. More specifically, the longitudinally opposite ends of the first elastic member 17 are bonded to the associated ends of the second elastic member 18 with use of said adhesive so that the respectively associated ends intersect each other or extend in contact with each other side by side. However, the hot melt type adhesive usually used to bond various components together in a diaper of this type presents insufficient bonding force, even after being applied and cured on these components, to resist said separation.

Figure 9:
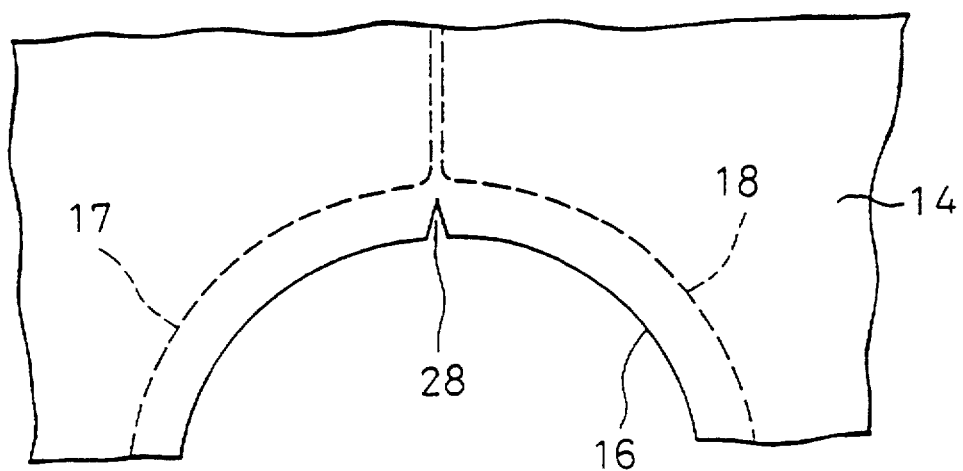

Though not shown, the longitudinally opposite ends of the first elastic member 17 may extend in parallel with the associated ends of the second elastic member 18 either in contact with each other or as shown in FIG. 9 even with a slight spacing, for example, of less than 10 mm, so that the entire peripheral edge of the opening 16 can be elastically contracted to form substantially uniform gathers. It is also possible without departure from the scope of the invention, though not specifically shown, to position the respective associated ends of the first and second elastic members, which may intersect each other, extending in parallel in contact with each other or extending with a slight spacing from each other at the middle points on the laterally opposite edges of the opening 16.

Between laterally opposite edges of the first topsheet 11 and laterally opposite edges of the backsheet 12 and at points outwardly from both sides of the liquid-absorbent core 13, a plurality of elastic members 19, each comprising, a plurality of elastic rubber threads, are attached in their stretched states, with use of hot melt type adhesive (not shown), respectively, so as to be stretchable longitudinally of the sheets and fit tightly around the user's legs. Similarly, between the longitudinally opposite ends of the first topsheet 11 and the associated ends of the backsheet 12, there are provided a plurality of elastic members 24 each comprising a plurality of elastic rubber threads, respectively, so as to be stretchable transversely of the sheets and fit tightly around the user's waist.

The first topsheet 11 may be made of nonwoven fabric, porous plastic film or the like. The backsheet 12 may be made of plastic film, or a laminated sheet of this plastic film and a nonwoven fabric or the like. The liquid-absorbent core 13 may be made of a mixture of fluff pulp and high absorption polymer powder or the like. The second topsheet 14 is preferably made of water-repellent and highly air-permeable nonwoven fabric. It should be understood that the term "liquid-resistant" material refers to the material having a sufficient degree of water-repellence to prevent liquid excretion from easily penetrating therethrough when the diaper is put on the user's body.

Referring to FIG. 1, the diaper 10 has two pairs of wing-like flaps 20 extending outward from the laterally opposite sides of the waist line, respectively, and the free ends of tape fasteners 21 attached to respective rear side wing-flaps 20 may be adhesively secured to the backsheet 12 to hold the diaper 10 around the user's body.

Methods for forming the opening 16 in the second topsheet 14 and providing this opening 16 with the first and second elastic members 17, 18 will be described in reference with FIGS. 4 and 5 which exemplarily illustrate a first method and FIGS. 6 and 7 which exemplarily illustrate a second method.

Figure 4:
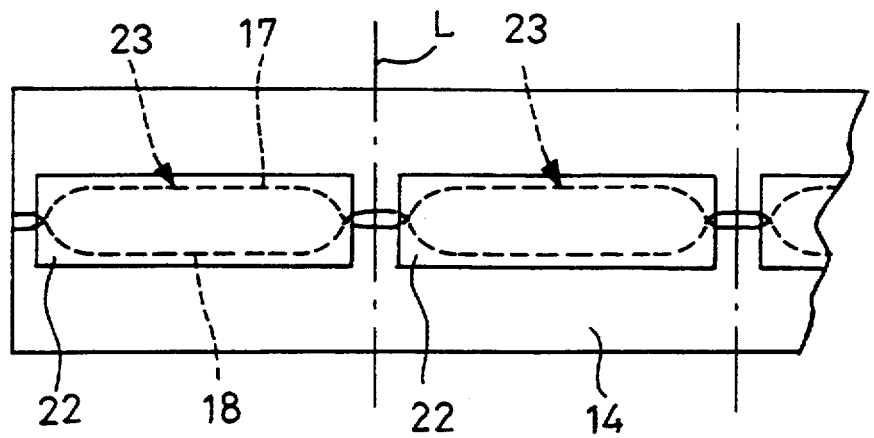
FIG. 4 is a plan view illustrating openings formed in the continuous second topsheet as well as the first step in the first method for attaching the elastic members to the peripheral edges of the respective openings.
Figure 5:
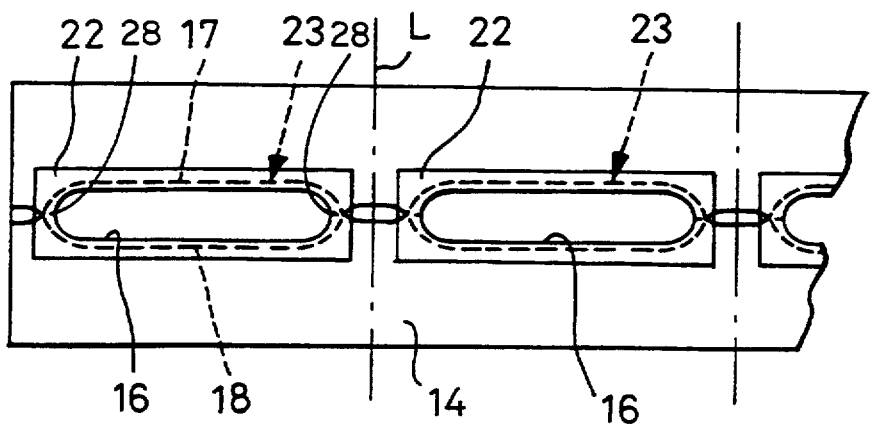
FIG. 5 is a plan view illustrating openings formed in the continuous second topsheet as well as the second step in the first method for attaching the elastic members to the peripheral edges of the respective openings.

Referring to FIG. 4, the continuous first and second elastic members 17, 18 being stretched by a predetermined elongation percentage are placed on the rear side of the second topsheet 14 along its central zone by a pair of traverse means (not shown) and simultaneously bonded thereonto with use of hot melt type adhesive so that these two elastic members periodically intersect each other at locations adjacent the longitudinally opposite ends of the individual diapers. A strip 22 of liquid-resistant nonwoven fabric sufficiently large to cover the length of the first and second elastic members 17, 18 is placed on the second topsheet 14 of each individual diaper and is bonded onto the second topsheet 14 by means of hot melt type adhesive. Thereafter, as will be apparent from FIG. 5, the second topsheet 14 and the strip 22 of nonwoven fabric are partially cut away along the line extending slightly inside an elastic annular line 23 defined by the first and second elastic members 17, 18 so as to form the opening 16 of a shape which is similar to the shape defined by said elastic annular line 23.

Figure 6:
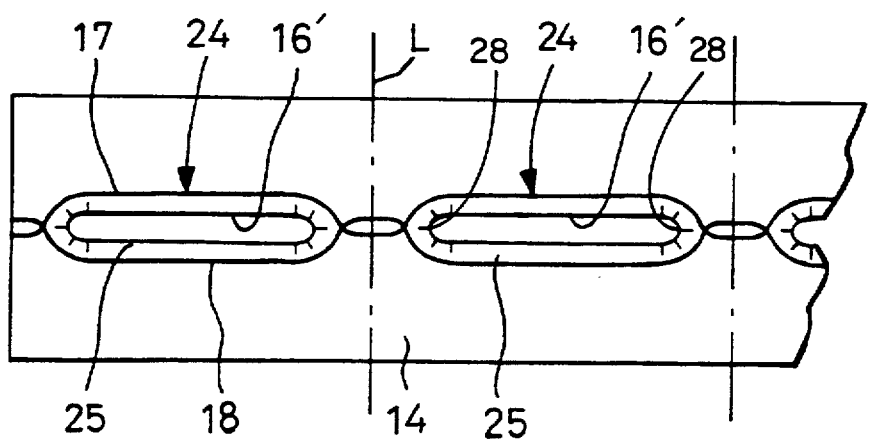
FIG. 6 is a plan view illustrating openings formed in the continuous second topsheet as well as the first step in the second method for attaching the elastic members to the peripheral edges of the respective openings.
Figure 7:
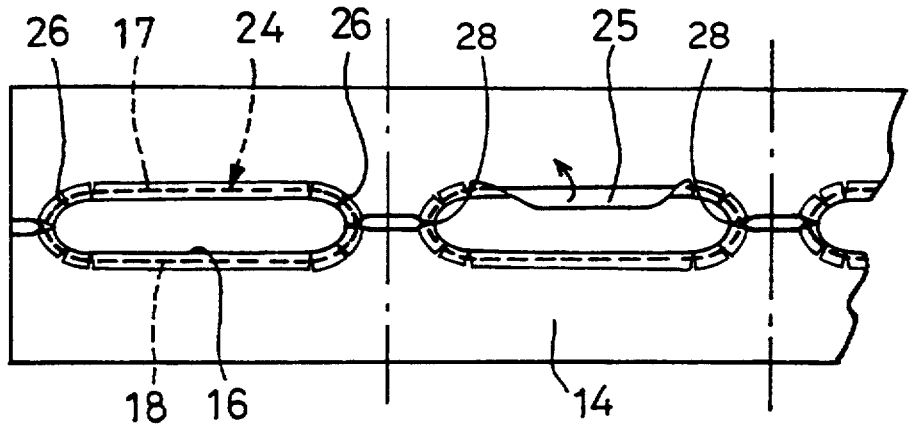
FIG. 7 is a plan view illustrating openings formed in the continuous second topsheet as well as the second step in the second method for attaching the elastic members to the peripheral edges of the respective openings.
Figure 8:
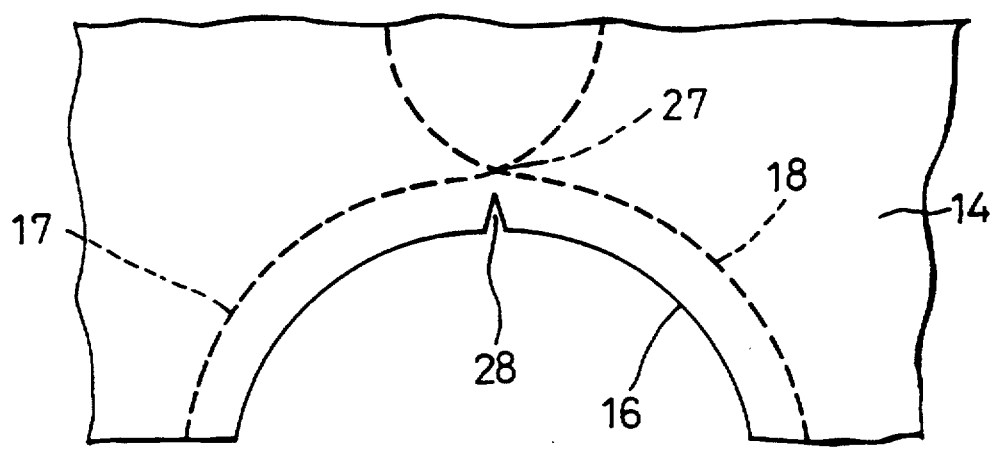
FIGS. 8 and 9 are views showing, on an enlarged scale, one of the longitudinally opposite ends of said opening and the region adjacent this end.

Referring now to FIG. 6, the continuous first and second elastic members 17, 18 being stretched by a predetermined elongation percentage are placed on the rear side of the second topsheet 14 along its central zone by a pair of traverse means (not shown) and simultaneously bonded thereonto with means of hot melt type adhesive so that these two elastic members periodically intersect each other at locations adjacent the longitudinally opposite ends of the individual diapers. Then, the second topsheet 14 is partially cut away along the line extending slightly inside an elastic annular line 24 defined by the first and second elastic members 17, 18 so as to form an opening 16 of a shape which is similar to that defined by said elastic annular line 24. Thereafter, as will be apparent from FIG. 7, a peripheral edge 25 extending inward from the elastic annular line 24 is folded back and bonded to the second topsheet 14 by means of hot melt type adhesive to cover the elastic annular line 24 and thereby to form the desired opening 16. To assure that the longitudinally opposite circular arc-shaped ends of the opening 16 can be neatly folded back during operation of folding back the peripheral edges, these circular arc-shaped ends are provided at regular intervals with notches 26.

Referring to FIGS. 4 through 7, reference letter L designates an imaginary lines along which the second topsheet 14 is cut to obtain the individual diapers. This operation of cutting is effected by cutting the continuous laminate into the individual diapers after such continuous laminate has been constructed (See the laminate 15 shown in FIG. 2). It should be understood that the lengths of the first and second elastic members 17, 18 extending between each pair of the adjacent elastic annular lines 23 (24) may be or may not be applied with adhesive and, if no adhesive is applied, these lengths of the elastic members 17, 18 are appropriately snapped back at the moment of said cutting.

The peripheral edge of the opening 16 is provided at positions opposed to and adjacent the respective intersections of the first and second elastic members 17, 18 with guide notches 28 for tearing off. This guide notch 28 is preferably provided at each of the longitudinally opposite ends of the opening 16 but may be provided at any one end. While such guide notch 28 is very effective to facilitate tearing off of the second topsheet 14, tearing off of the second topsheet 14 can be further facilitated preferably by orienting the component fibers of the second topsheet 14, when the latter is made of nonwoven fabric, in the direction along which the guide notch is to be torn off, for example, longitudinally of the diaper in the embodiment shown.

While so-called open type diaper using the tape fasteners to close the waist line has been illustrated and described as a specific embodiment, the invention will be applicable also to so-called pants type diaper (inclusive of training pants) having a continuous waist line.

Liquid excretion is absorbed through the opening 16 and then the first topsheet 11 into the core 13 while solid excretion flows into a pocket defined between the first topsheet 11 and the second topsheet 14. Such solid excretion may be scraped away, if necessary, after the second topsheet 14 has be torn off from the guide notch 28 to expose the first topsheet 11 over an adequate extent.

According to the invention, the first and second elastic members are independently attached on the second topsheet substantially along the respective halves of the opening, respectively, so that substantially the entire peripheral edge of the opening is elasticized by these first and second elastic members. Nevertheless, as will be appreciated from the foregoing description, these first and second elastic members are not continuous with each other but intersect, contact or closely approach each other at their longitudinally opposite ends. Such arrangement allows the longitudinally opposite ends of the first and second elastic members to be easily separated from each other as the second topsheet is torn off from the locations adjacent these ends in order that the first topsheet underlying the second topsheet can be exposed and thereby solid excretion clinging to the first topsheet can be scraped away.

The above-mentioned operation of tearing off the second topsheet is facilitated by provision of the guide notch for such tearing off into the edge portions of the opening adjacent the locations at which the longitudinally opposite ends of the first and second elastic members intersect, contact or closely approach each other and further facilitated by orienting most of the component fibers of nonwoven fabric used as the material of the second topsheet in the direction along which the guide notches are to be torn off.

What is claimed is:

1. A disposable diaper in the form of an integral laminate comprising
   (a) a liquid-permeable first topsheet (11), a liquid-impermeable backsheet (12), a liquid absorbent core (13) sandwiched between said first topsheet (11) and said backsheet (12), and
   (b) a liquid-resistant second topsheet (14)
      (1) overlying said first topsheet (11) and having an outer periphery that is bonded to said first topsheet (11),
      (2) having longitudinal and transverse directions and a central zone located inwardly of said outer periphery,
      (3) having an opening (16) in said central zone which extends longer in said longitudinal direction than in said transverse direction, said opening (16) having a periphery and longitudinally opposite ends, and
      (4) having a first elongated elastic member (17) attached adjacent one-half of said periphery of said opening (16), and a separate second elongated elastic member (18) attached adjacent the other half of said periphery of said opening (16), said first and second elastic members (17,18) having longitudinally opposite ends that intersect each other at the longitudinally opposite ends of said opening (16),
      (5) notches (28) in said periphery of said opening (16) to facilitate the tearing away of said second topsheet (14) so as to permit greater access to said first topsheet (11), said notches (28) being located adjacent to the point where the longitudinally opposite ends of said elastic members (17,18) intersect each other at the longitudinally opposite ends of said opening (16), respectively.

2. A disposable diaper as recited in claim 1, wherein said notches having a direction along which the notches are to be torn and said second topsheet (14) is composed of nonwoven fabric wherein the component fibers thereof are oriented in the same direction as said direction of said notches (28).

* * * * *